United States Patent [19]

McLachlan

[11] 4,419,365

[45] Dec. 6, 1983

[54] METHOD OF TREATING ALZHEIMER'S DISEASE

[75] Inventor: Donald R. McLachlan, Toronto, Canada

[73] Assignee: Ciba-Geigy Corporation, Ardsley, N.Y.

[21] Appl. No.: 332,794

[22] Filed: Dec. 21, 1981

[51] Int. Cl.$^{3}$ .................... A61K 31/16

[52] U.S. Cl. .................... 424/320

[58] Field of Search .................... 424/320

[56] References Cited

FOREIGN PATENT DOCUMENTS 1123436 2/1962 Fed. Rep. of Germany .
1163337 9/1964 Fed. Rep. of Germany .
1186076 10/1965 Fed. Rep. of Germany .
1898 7/1963 France .

OTHER PUBLICATIONS

Crapper et al., Science, vol. 180, pp. 511-513 (1973).
Crapper et al., Brain, vol. 99, pp. 67-80 (1976).
Pekl et al., Science, vol. 208, pp. 297-299 (1980).
McDermott et al., The Lancet, pp. 710-711 (Oct. 1, 1977).
Crapper et al., Brain Research, vol. 97, pp. 253-264 (1975).
Crapper et al., The Aging Brain and Senile Dementia, pp. 229-246 (1977).
Ackrill et al., The Lancet, pp. 692-693 (9/27/80).
Yunice et al., Arch. Environ. Health, pp. 163-170 (vol. 16-2/68).
Krishnan et al., Canadian Journal of Spectroscopy, vol. 21, No. 1, (Jan./Feb. 1976).
Müller, Conf. Proceed. St. Louis; Senile Dementia, pp. 237-250 (3/22-23/1978.
Crapper et al., Aging, vol. 7, pp. 471-485 (1978).
Trapp et al., Biological Psychiatry, vol. 13, No. 6, pp. 709-718 (1978).
Alfrey et al., New Eng. Jour. Med., vol. 294, No. 4, pp. 184-188 (1/22/76).

*Primary Examiner*—Stanley J. Friedman
*Attorney, Agent, or Firm*—Michael W. Glynn

[57] ABSTRACT

The present invention provides a method of treating Alzheimer's disease, which method comprises administering to a person requiring such treatment, a pharmaceutically acceptable acid addition salt of deferoxamine USAN. Such salts are preferably administered parenterally in the form of aqueous solutions. The dosage of suitable acid addition salts of deferoxamine, e.g. of the mesylate, is conveniently from about 0.2 to 5 g daily, preferably from about 0.2 to 1.5 g and in particular about 0.5 to about 1.0 g daily, especially twice daily 0.5 g, depending on the individual condition of the patient and the stage of the disease.

6 Claims, No Drawings

METHOD OF TREATING ALZHEIMER'S DISEASE

Alzheimer's disease is the most common cause of senile brain disease and is a relentlessly progressive, fatal and untreatable condition. The disease usually begins with learning-memory deficits and slowly progresses to involve all aspects of intellectual activity including judgment, calculation and language. Motor function is also progressively impaired. At variable intervals following the appearance of motor dyspraxia, there is a general increase in muscle tone of an extrapyramidal type and bradykinesia. As the disease progresses, tone increases in intensity, particularly in the flexor groups, resulting in a terminal state of posture in flexion. Myoclonic jerks may be present and seizures occur in perhaps 5–15% of affected individuals. The average duration of the illness is 8 years with a range between 2 and 19 years.

Aluminum has been recognized as a selective neurotoxic agent for over 90 years. Among the human neurological conditions associated with elevated brain aluminum are e.g. Guam and Kii peninsula (Japan) amyotrophic lateral sclerosis (spinal cord and brain); aged human brain; dialysis encephalopathy; striato-nigral syndrome; alcohol dementia with patchy demyelination and crystalline deposits; and Alzheimer senile and presenile dementia [cp. D. R. Crapper et al., Aluminum neurofibrillary degeneration and Alzheimer's disease, Science 180, 511–513 (1973), Brain 99, 67–80 (1976), G. A. Trapp et al., Aluminum levels in brain in Alzheimer's disease, Biol. Psych. 13, 709–718 (1978)]. Aluminum was found in the nuclei of neurons with neurofibrillary degeneration by D. P. Perl and A. R. Brody, Science 208, 297–309 (1980). J. R. McDermott et al., Aluminum and Alzheimer's disease, Lancet 1977, Vol. 2, 710–711, found brains of patients with senile dementia of the Alzheimer type to contain elevated concentrations of aluminum however, control brains of age-matched elderly persons also contained elevated concentrations of aluminum and the difference between the groups was not significant. As shown by D. R. Crapper McLachlan et al., Neurotoxicology 1, 25–32 (1980), the discrepancy appears to lie in the selection of the controls, since the brains of the age-matched control group had neurofibrillary degeneration of a density approaching that found in the Alzheimer group.

In susceptible test animals, such as cats and rabbits, after the intracranial injection of a single lethal amount of a soluble salt of aluminum a sequence of events occurs which begins with a learning memory deficit and ends with myoclonic jerks and seizures 14 to 28 days after the injection. The affected brains contain neurons with neurofibrillary degeneration. This sequence, despite the extremely short time course remarkably mimics the progression of signs found in Alzheimer's disease. Furthermore, the toxic concentration of aluminum in susceptible species ranges between 4 and 8 μg/g dry weight. [cp. D. R. Crapper and G. Tomko, Brain Research 97, 253–264 (1975)]. It is therefore of special interest that the aluminum concentration of 585 samples from the brains of 10 persons who died of Alzheimer's disease determined by D. R. Crapper et al., Brain 99, 67–80 (1976), overall was 3,8 μg/g dry weight, and in approximately $\frac{1}{3}$ of all neurocortical regions exceeded 4 μg/g dry weight. In addition, human cerebral fetal neurons in vitro show a toxic response to aluminum at the same concentrations as the susceptible animal species [cp. D. R. Crapper et al., in Aging, Vol. 7, pages 471–485, edited by R. Katzman et al., Raven Press, New York (1976)].

The intracellular distribution of aluminum in both the experimental encephalopathy associated with neurofibrillary degeneration as well as in Alzheimer's disease is almost exclusively intranuclear. Within the nuclear fractions aluminum is not equally distributed. Based on sedimentation profiles, D. R. Crapper and U. DeBoni (in K. Nandy and J. Sherwin, Editors: The Aging Brain and Senile Dementia, Plenum Press, New York and London 1979, pages 229–246) separated a heavy fraction, heterochromatin, and two lighter fractions, intermediate euchromatin and light euchromatin, from the nuclei of brains of control cats and cats killed during the advanced stages of the experimentally induced aluminum encephalopathy. Quantitative measures of aluminum by atom absorption and of DNA by standard methods revealed that nuclei of control brains contain about 700 μg aluminum per g of DNA, and in the heterochromatin fraction about 1550 μg/g DNA. In the encephalopathic brains, these concentrations were increased by about 370% and 540% respectively. According to D. R. Crapper et al., Brain 99, 67–80 (1976), brains of patients with presenile Alzheimer dementia (6 brains, 11 preparations) had average concentrations of aluminum of 1401 and 3783 μg Al/g DNA for total nuclei and heterochromatin, respectively, compared to 716 and 2111 μg/g DNA of age-matched control brains (6 brains, 11 preparations), corresponding to an approximately twofold increase in the intranuclear content of aluminum.

Despite the above named similarities between Alzheimer's disease and experimental encephalopathy induced by intracranial injection of aluminum ions, it can be assumed that the primary events which initiate Alzheimer's disease consist in the reduction of the defences of the brain to the naturally occuring toxic aluminum rather than in an excessive supply of aluminum ions. The latter, however, is recognized as the cause of the dialysis encephalopathy, an entity distinctly different from Alzheimer's disease. The differences are that in dialysis dementia there are no histopathological brain changes. All tissues of the body have high aluminum levels, i.e. about 10 to 20 times normal, but in the brain, the aluminum is restricted to the cytoplasm and is excluded from the nucleus. In contrast thereto, in Alzheimer's disease there is extensive histopathology including neurofibrillary degeneration, the aluminum is almost totally bound to intranuclear structures and the brain is the only organ affected. Alzheimer's disease therefore closely resembles experimental animal encephalopathy. Dialysis encephalopathy has become rare after care has been taken everywhere to ensure that the aluminum content of dialysis water is kept to a minimum. The striking improvement of the condition of a patient, afflicted with dialysis encephalopathy, after removal of a substantial quantity of aluminum by infusing 6 g of the pharmaceutical chelating agent desferrioxamine mesylate (BAN, corresponding to deferoxamine mesylate USAN and INN prop.) in 500 ml of saline water into the arterial line during the first two hours of a dialysis, once weekly over a period of 10 months, is reported by P. Ackrill et al., The Lancet 1980, Vol. 2, 692–693. According to P. Williams, R. Khanna and D. R. Crapper MacLachlan, Bulletin of Dialysis 1, 73 (1981) aluminum excretion was also enhanced by deferoxamine in a patient on continuous ambulatory peritoneal dialysis who suffered from dialysis dementia. Before it had been known from A. A. Yunice et al., Arch. Envir. Health 16, 163–170 (1968), that in rats maintained on deferoxamine USAN for four months aluminium is reduced on lung, pancreas, heart muscle and brain and the animals exhibited no toxic effect.

The present invention provides a method of treating Alzheimer's disease, which method comprises administering to a person requiring such treatment, a pharmaceutically acceptable acid addition salt of deferoxamine USAN (desferrioxamine BAN, chemical name N-[5-[[4-[[5-(acetylhydroxyamino)pentyl]amino]-1,4-dioxobutyl]hydroxyamino]-pentyl-N-(5-aminopentyl)-N-hydroxybutanediamide or 30-amino-3,14,25-trihydroxy-2,10,13,21,24-pentaoxo-3,9,14,20,25-pentaazatriacontane). Such salts are preferably administered parenterally in the form of aqueous solutions. The dosage of suitable acid addition salts of deferoxamine, e.g. of the mesylate, is conveniently from about 0.2 to 5 g dialy, preferably from about 0.2 to about 1.5 g and in particular about 0.5 to about 1.0 g daily, especially twice daily 0.5 g, depending on the individual condition of the patient and the stage of the disease.

Suitable formulations for the treatment of Alzheimer's disease are, in particular, 2.5 to about 12.5%, preferably 5 to about 10%, aqueous solutions of pharmaceutically acceptable acid addition salts of deferoxamine, which solutions have been freshly prepared, or shortly beforehand, from dry ampoules, or from other stable and sterile stored formulations of the particular salt, and distilled or demineralised water. For example, 10% or even less concentrated solutions of deferoxamine mesylate can be prepared using the commercially available 500 mg dry ampoules of DESFERAL$^R$ (registered trademark of CIBA-GEIGY AG) and e.g. distilled water or physiological sodium chloride solution. Such solutions can be administered parenterally, e.g. by intramuscular injection, e.g. into the glutaeus maximus, or into the anterior thigh muscles or the deltoid muscle, further by intravenous or subcutaneous injection or by infusion. Suitable especially for self-administration or administration by non-qualified persons, e.g. at home or in homes for the aged, is a slow subcutaneous injection, e.g. into the abdominal skin, using a portable infusion pump and a flexibly mounted syringe, over the course of several hours one or twice daily or continuously throughout the day or night, in the manner employed for the known treatment of diseases characterized by pathological iron overload with pharmaceutically acceptable acid addition salts, especially the mesylate, of deferoxamine, such as for the treatment of haemochromatosis, for example in the case of diseases the treatment of which requires periodic blood transfusions, such as thalassaemia.

Acid addition salts of deferoxamine can be administered as the sole specific medicament against Alzheimer's disease or together with concomitant and/or alternative administration of other medicaments, which are recognized to have beneficial effects in Alzheimer's disease, such as, e.g. tetracycline, sodium fluoride, calcium lactate-gluconate or other calcium salts, vitamin D3 and/or ascorbic acid. Alternation may take place, e.g. every week, every second week or every month, or an acid addition salt of deferoxamine may be administered for three weeks and thereafter another medicament for one week. While the treatment thus may be interrupted for short periods of time, especially if other beneficial medicaments are administered meanwhile, it should be continued in the long run substantially during the lifetime of the patient.

The preparation of deferoxamine and of pharmaceutically acceptable salts, in particular the hydrochloride (m.p. 171°–173° C.), is described in German patent specification No. 1,186,076 (Examples 1 and 2, designated as desferri-ferrioxamine B-hydrochloride). The preparation of the ferrioxamine B-hydrochloride, used as starting material, from plant material is described in German patent specification No. 1,123,436; and the synthesis of desferrioxamines is described in German patent specification No. 1,163,337. Further salts, such as the mesylate already referred to (methane-sulfonate, m.p. 140°–142° C.), the sulfate (m.p. 170°–172° C.) and the tartrate (m.p. 159°–161° C.), are described in French patent specification No. 1,898 M. Also described in this publication is the preparation of pharmaceutical formulations, i.e. dry ampoules, suppositories and capsules, which contain such salts. Further suitable salts are those referred to in German patent specification No. 1,186,076, including e.g. those with phosphoric acids, acetic acid, glycollic acid, lactic acid, succinic acid, maleic acid, fumaric acid, malic acid, tartaric acid, citric acid, ethanesulfonic acid and hydroxyethanesulfonic acid.

According to new measurements by hydrogen titration, deferoxamine has a stability constant for aluminum binding of $10^{21-23}$ and for iron binding of $10^{30-31}$. This is in agreement with prior indications, c.p. H. Keberle, The biochemistry of desferrioxamine and its relation to iron metabolism, New York Academy of Sciences, Symposium on Iron, pages 758–764, 1963.

The results of the following study show the beneficial effect of the treatment of Alzheimer's disease by parenteral administration of deferoxamine mesylate.

Three independent measures of cerebral function were selected as measured of the clinical course: repeated measures of cognitive performance as measured by the Wechsler Adult Intelligence Scale and the Wechsler Memory Scale, repeated measures on a signal detection task involving a backward masing paradigm and repeated measures to electroencephalographic slow wave abnormality employing power spectral analysis.

METHODS

A. Criteria for the Clinical Diagnosis of Alzheimer's disease

For the purpose of this study, the diagnosis of Alzheimer's disease required evidence, presented by reliable observers, of examples of impaired memory performance and other cognitive functions together with personality change over at least a periode of 24 months. Included in the history was convincing evidence of an insidious onset and steady progression in the severity of the cognitive deficits. Patients were excluded from the study with a history of transient ischemic attack, stroke, uncontrolled hypertension, renal disease, peptic ulcer requiring aluminum containing antacids or any other systematic illness. Patients with a history of a head injury with prolonged unconsciousness, alcohol or drug abuse or depression were excluded. Patients with a family member who developed progressive memory deficits prior to the age of 70 or who had familial neurological disorders of any type were excluded. No patients with an occupation history of aluminum welding, grinding or inhalation of aluminum oxide for prophylactic purposes were included.

The physical examination required evidence of memory impairment together with evidence of cerebral hemisphere involvement such as spatial disorientation, dysphasia, or motor dyspraxia in the presence of clear consciousness. Neurological signs of the more advanced stages of Alzheimer's disease, such as the palmomental reflex, hyperactive facial reflexes and impaired upward gaze were rarely present when patients entered the study, although they invariably appeared later in the course of the illness. For inclusion in the study, the remainder of the physical examination was entirely normal including blood pressure. Routine blood and urine tests were normal as well as the electrocardiogram. A CT scan of the brain revealed cerebral atrophy in all cases. Re-examination at 6–18 months had to reveal evidence of progressive changes in the major criteria for the initial diagnosis. From a group of over 100 patients living at home complaining of memory disorders, 17 met the selection criteria. They also came from the same socioeconomic strata, with comparable levels of education and occupational backgrounds. Each of these patients had the benefit of a caring relative and each was living at home under essentially identical environmental conditions and overall health was comparable. Of the 17 patients, 6 randomly selected patients, 3 males and 3 females, were given deferoxamine mesylate which in the following is referred to as deferoxamine, by intramuscular injection of its aqueous solution. Placebo treatment of the 11 control patients, comprising daily intramuscular injections, over about two years appeared to be unethical, besides, a sustained placebo effect in the treated group for 6 to 23 months is unlikely.

To estimate the accuracy of clinical diagnosis, another group of patients with dementia were examined concurrent with the group selected for detailed clinical study. The clinical diagnosis of Alzheimer's disease was assigned and post-mortem examination was obtained on 41 of these individuals. Brains were bisected in the midsaggital plane and one-half fixed in neutral buffered formalin for 14 days. Extensive histopathological examination was carried out employing hematoxylin-eosin and Bielschowsky's stains and electronmicroscopy. The pathological diagnosis required widespread and numerous neurons with neurofibrillary degeneration and neuritic, senile, plaques in the neocortex and hippocampal region. Histopathological examination revealed typical Alzheimer's disease in 36 of the 41 patients.

B. Measures of the Clinical Course (1) Measures of Cognitive Function Including Memory: The Wechsler Adult Intelligence Scale and Wechsler Memory Scale form 1 were selected as measures of cognitive function. These instruments were employed at intervals of 4–18 months and were delivered by the same examiner.

(2) Signal Detection Task Employing a Backward-Masking Paradigm. Visual information processing capabilities of the patients were examined employing M. T. Turvey's (1973) signal detection backward visual masking tests [cp. Psychol. Review, 80, 1–52 (1973)]. Performance on these tests is generally assumed to reflect the activity of those central brain processes involved in the analysis of visual features and pattern recognition rather than the simple transmission of information to the brain [e.g., Till and Franklin, J. Gerontol, 26, 200–210 (1980)].

The apparatus consisted of a three-channel Pandora's-box tachistoscope in which single, binocular, letter stimuli (½-inch Franklin Gothic-style stick-letters A,H,T,O,U,W,X and Y) subtending 1° visual angle were presented to the persons when dark-adapted to a background luminance of 20 cd/m$^2$. Contiguous with the "off" of the letter stimulus was a 30 msec "pattern mask" presented at a luminance of 170 cd/m$^2$. Photometric measurements were made with Tektronix digital photometer with a J6503 luminance probe. The pattern mask was made of segments of the letter stimuli, "I" and "T" randomly aligned and overlapped the entire area of the letter stimulus presentation field. The interval between letter stimulus off and pattern mask onset (the interstimulus interval) was set at zero throughout. Only the duration of the letter stimulus was varied in 1–5 msec steps over the expected range of performance from 1–999 msec.

The recognition threshold for letter stimuli was defined as that duration of letter stimulus presentation at which the patient could correctly identify four consecutive letter presentations in the absence of the masking stimulus. Each person was required to reach this criterion in order to be presented with a backward pattern-mask test procedure. Failure to establish a recognition threshold for the letter stimuli was used as the decision rule for terminating the test. The identification threshold was defined and measured similarly to the recognition threshold except that it was obtained when the letter stimuli were followed by the pattern mask and after the recognition threshold had been previously established. Visual acuity for both eyes as well as a visual performance profile were obtained using a Bausch and Lomb Modified Ortho-rater and the standard clinical practise outlined for its use in the manual.

(3) Quantitative Measures of Electroencephalographic Slow Wave Disorganization. Employing standard leads (C3-Pz:C4-Pz) two channels of the electroencephalogram were digitized under the control of a CAMAC [cp. Barnes and Hooton, U.K. Atomic Energy Authority Research Group Reports, (1969)] crate and PDP 11/05 computer from a Grass Model 8 polygraph with band pass filters set between 1 and 70 Hz. Subjects were recumbent with their eyes closed while a 12 second epoch was sampled at 128 samples per second. Five or six epochs were collected at random intervals within a total observation period of 30–45 minutes. The subjects were maintained in a relaxed and attentive state and the measurements were all made by the same person. The resultant time series were operated on by an algorithm for the Fast Fourier Transform to generate the corresponding spectral distributions expressed in one cycle frequency increments. Any region of artifact was deleted from analysis. For statistical analysis the theta band was defined as the sum of power in the range of 4–7 Hz and the alpha band was the sum of power in the range of 8–12 Hz. The ratio of these two bands, the theta to alpha ratio, was employed as an index of electroencephalographic abnormality.

C. Deferoxamine as an Aluminum Chelator

To establish that aluminum excretion is increased by deferoxamine in patients with Alzheimer's disease, 5 individuals were admitted to hospital and placed on a standard hospital diet for 48 hours. None had a history of using aluminum containing antacids. Following the initial period of standard diet, urine collection was carried out for 12 hour intervals employing plastic, acid-washed, aluminum-free containers. Following three days of control urine collection the patients received 500 mg of intramuscular deferoxamine at 8 am and at 8 pm. Aluminum measured in the urine by atomic absorption spectroscopy, employing a Perkin Elmer model 305B unit equipped with a deuterium background corrector and the Perkin Elmer HGA2000 graphite furnace [cp. Krishnan, Quittkat and Crapper, Can. J. Spectroscopy 21, 25–30 (1976)].

RESULTS

Based on the examination of the clinical diagnosis of Alzheimer's disease in a separate group of patients reported above, the diagnostic accuracy in the selected cases of this report is conservatively estimated to be about 86% correct. Accordingly, only two cases out of the 17 of this report are likely to have a progressive dementia of a type other than Alzheimer's disease. However, four cases have already been histopathologically verified as shown in Table 1.

(A) Deferoxamine and Urinary Aluminum Excretion

Five patients with Alzheimer's disease were admitted initially to hospital and the urinary excretion of aluminum measured while on standard hospital diet during 3 control days and during 3 days of 500 mg intramuscular deferoxamine delivered at 12-hour intervals. The results are shown in Table 5 and indicated that intramuscular deferoxamine results in a 270 percent increase in urinary aluminum excretion. Subcutaneous infusion of 1 g over each 24-hour period did not result in excretion of larger amounts of aluminum.

(B) Cognitive Function in Alzheimer's Disease

Although there is considerable variation, repeated measures of cognitive performance on the Wechsler Adult Intelligence Scale and Memory tests at 4- to 9-month intervals indicated that the overall trend is for scores to decrease. Sixty-eight data points were available for 12 selected ambulatory patients living at home (Table 1). The average age at which the patients entered the study was 61±7 SD years and they were first considered by a reliable witness to have exhibited symptoms at a mean age of 57±7 SD years. They were on no medications. The probability that test scores declined compared to those which remained unchanged or improved is shown in Table 2. Assuming that test score differences of 3 or more points are likely to represent meaningful trends in cognitive performance, the probability of deterioration when measured at a mean interval of 8.8±4.2 SD months was 0.80 for Verbal I.Q. scores, 0.75 for Performance I.Q. scores and 0.87 for Memory scores. There were no improved Verbal I.Q. scores and a 0.05 probability was established for improved Performance I.Q. and Memory scores between repeated measures.

The average rate of decline was highly variable from patient to patient and within repeated measures taken from single patients (Table 1). Expressing data as a change in score points per month between test intervals, an average rate of change for Verbal I.Q., Performance I.Q., and Memory scores was −0.81, −0.83, and −0.57 points/month respectively. However the standard deviations were large, 0.59, 0.77 and 0.48 respectively, indicating a wide range of rates of decline even for inter-test intervals for the same patient. Furthermore, attempts to relate the date of onset of changes in cognitive function or personality change to the I.Q. scores revealed no correlation even when normalized on the assumption that the average initial I.Q. of this group of patients was set at either 100 or 120. The Wechsler Intelligence Scale and Memory tests were useful for not more than 2.5 years after initial diagnosis or on the average for about 6.5 years after the onset of observed changes in the cognitive function.

(C) Deferoxamine and Altered Cognitive Function

The six randomly selected patients with Alzheimer's disease, 3 males and 3 females, who were given deferoxamine had an average age at first diagnosis of 57±4 SD years and were first noted to have altered cognitive function by a reliable witness at an average age of 53±4 SD years. These patients were maintained on intramuscular deferoxamine for 6 to 23 months according to the schedules shown in Table 1B. Compared to the test scores of the 11 closely matched untreated controls, and the pretreatment scores of one of the treated group, the 6 treated patients have fewer scores which reveal deterioration: 0.67 for each of the Verbal I.Q., Performance I.Q., and Memory scales compared to 0.80, 0.75 and 0.87 respectively for the untreated group, (Table 2). The treated group had a larger proportion of scores which exhibited either no change or improvement. For Verbal I.Q., Performance I.Q., and Memory scores the probability of no change or improvement taken together for the treated group was 0.39, 0.34, and 0.35 respectively compared to 0.20, 0.25, and 0.13 for the untreated group.

Examination of the individual test scores in Table 1B revealed that patients treated for 12 to 23 months exhibit the least change. In both patients 12 and 13 a dramatic drop in performance was encountered 6 months after treatment was discontinued. The Verbal I.Q., Performance I.Q., and Memory scores for patient 12 were 60, 95 and 62 respectively prior to treatment and 60, 89 and 64 respectively for the 2 years on treatment. Six months after treatment was discontinued the scores dropped to 46, 68, and 48 respectively. Similarly for patient 13 the scores during treatment were 72, 59, and 52 and 6 months after treatment was discontinued the scores were 57, 53 on the I.Q. tests and performance was untestable on the Wechsler Memory test. Patient 14 remains on treatment and test scores have exhibited no change or a small decline. While on treatment the families of these patients reported little if any loss in cognitive function. In constrast, the families of patients 12 and 13 noted rapid deterioration after the medication was terminated. The 3 patients treated for only 6 months continued to decline on these tests.

(D) Signal Detection Task Employing Backward Masking

Table 3 is a summary of the Identification Thresholds obtained during the backward pattern mask condition for six untreated control patients and five patients treated with deferoxamine. The values of Table 3 were obtained as follows: for all patients the "before" values were the initial scores obtained in the test. For the treated patients the "during" values were computed from an average of all values obtained within the treatment period (average 313 days) and the "during" values were computed in a similar manner for the comparable time interval for the control patients (average 304 days).

All 6 untreated control patients showed either no change or an increase (deterioration) in the identification threshold measurement made in the pattern mask condition. The average change in identification threshold for the controls was 20 msec when measured at an average inter-test interval of 304 days (range 120 to 484 days). This difference approaches statistical significance ($0.05<p<0.10$, $t=1.97$, with df=5) when Student's "t" test for correlated sample means is performed and indicates loss of function during the 10 month interval.

Two out of the five treated patients showed a decrease in threshold (improvement when scores were compared before treatment to those obtained during treatment. Student's "t" for correlated samples indicated that the changes in the treated group for a time interval comparable to the control group were not statistically significant ($t<0.10$, df=3); as a group, these patients did not lose function while on treatment.

(E) Electroencephalographic Alterations

H. Berger [Electroenceph. clin. Neurophys. sppl. 28, 151–171 (1932)] and others [cp. Crapper, Dalton, Skopitz, Scott and Hachinski, (1976), H. F. Muller, Senile dementia, a biomedical approach, ed. by K. Nandy, Elsevier, North-Holland Biomedical press, 237–250, (1978)] reported progressive slow wave disorganization in primary parenchymal brain degenerations which correlated approximately with the progressing cognitive deficits. Repeated measures of theta to alpha ratio, taken at intervals of 6–12 months and based upon 58 recordings on 15 patients on no medication, Table 1, also demonstrates a correlated trend ($r=0.51$) with the estimated onset of illness, FIG. 1. As the electroencephalographic abnormality becomes more profound there is an increased variability in the resting waveforms. The theta to alpha ratio was chosen as a parameter for study because this ratio not only reflects the amount of diffuse slow wave activity but has small intraindividual variability from day to day. To establish the variability in the theta to alpha ratio for 5 Alzheimer affected individuals, 28 repeat recordings were made with a modal inter- observational period of 3 days. The standard deviation in theta to alpha ratio was employed to calculate an average standard deviation for the group and was found to be $0.10\pm0.04$ SD. The value is approximately three times greater than the value obtained for healthy control individuals of $0.03\pm0.01$ (aged 26, 32, 65 and 77 years) for 16 recording sessions.

(F) Effect of Deferoxamine on the Electroencephalogram

To examine for an effect of deferoxamine upon the $\theta:\alpha$ ratio, data are categorized into three states: improved, no change or deteriorated. The criteria for categoriation was based on a change in the ratio of greater than 0.10 (one standard deviation for interobservation variability for the Alzheimer patients), between any two observations made at intervals of 6–18 months. The probability of each of these states was computed for each patient and then averaged and the results are shown in Table 4. Independent of the hemisphere from which the data was obtained, an Alzheimer patient not receiving deferoxamine has a 0.79 probability of displaying an increase in the theta to alpha ratio. This probability of EEG deterioration is reduced in the deferoxamine treated group of 6 patients to 0.25. For the treated group the most probable state was that of no EEG change: 0.50 in the treated group compared to 0.20 in the untreated group. Even in the 3 patients who received deferoxamine for only 6 months and failed to exhibit alterations in cognitive function, the EEG exhibited either stabilization or improvement and these individual values are given in Table 1B.

(G) CONCLUSION

Taken as a group, the six patients treated with deferoxamine revealed a decline in brain function, as measured by each of the three criteria employed, much less than that observed in a comparable test interval for the untreated group of eleven patients. As shown in Table 1B, administration routines ranged between 0.5 g at 12 hour intervals each day to 0.5 g each day for 28 days followed by 28 days without deferoxamine. In view of the minimal side effects observed in this study, the more appropriate schedule appears to be continuous intramuscular injections of 0.5 g at 12 hour intervals.

The present invention also relates to pharmaceutical preparations for use in the method claimed herein, and to the production thereof. French patent specification No. 1 898 M referred to above describes the preparation of dry ampoules, suppositories and capsules. Dry ampoules containing other pharmaceutically acceptable acid addition salts of deferoxamine, in particular the methanesulfonate (mesylate), as active ingredients, and also containing other amounts of active ingredients, can also be prepared.

The pharmaceutical preparations are sterilized and can contain adjuvants e.g. preservatives, stabilizers, wetting agents and/or emulsifiers, solubilizers, salts for regulating the osmotic pressure and/or buffers. These pharmaceutical preparations are formulated in known manner, e.g. by conventional mixing, dissolving and lyophilizing methods.

EXAMPLE

Dry ampoules containing 250 mg of active ingredient for the preparation of 10% or 5% aqueous solutions are prepared by pouring 2.5 ml of a 10% solution of deferoxamine mesylate into dry ampoules for 2.5 ml and 5 ml, respectively, of ready-for-use solution and lyophilizing in a conventional manner. The solutions used for the lyophilization can also additionally contain 8% of mannitol, corresponding to 200 mg per ampoule.

TABLE 1A

Patient Data Summary

| Patient | Sex | Age of Onset | Age at First Observation | Day of Observation | WAIS Verbal | WAIS Performance | Wechsler Memory | Backward Masking (msec) | Theta:Alpha C3-Pz | Theta:Alpha C4-Pz |
|---|---|---|---|---|---|---|---|---|---|---|
| 01 | F | 50 | 55.5 | 0 | 101 | 95 | 83 | 80 | 1.38 | 1.33 |
| | | | | 196 | — | — | — | 115 | — | — |
| | | | | 358 | 95 | 82 | 72 | — | — | — |
| | | | | 484 | — | — | — | 120 | 1.32 | 1.35 |
| | | | | 644 | 89 | 66 | 57 | 110 | 1.62 | 1.52 |
| | | | | 868 | 74 | 55 | 51 | 150 | 2.29 | 2.12 |
| | | | | 1308 | — | — | — | nt | nt | nt |
| 02 | M | 52 | 56 | 0 | 125 | 102 | 81 | — | 0.96 | 0.90 |
| | | | | 216 | 122 | 99 | 76 | 100 | 0.97 | 1.02 |
| | | | | 502 | 114 | 96 | 69 | 160 | 1.28 | 1.21 |

TABLE 1A-continued

Patient Data Summary

| Patient | Sex | Age of Onset | Age at First Observation | Day of Observation | WAIS Verbal | WAIS Performance | Wechsler Memory | Backward Masking (msec) | Theta:Alpha C3-Pz | Theta:Alpha C4-Pz |
|---|---|---|---|---|---|---|---|---|---|---|
| 03 | F | 53 | 55 | 0 | 99 | 65 | 73 | — | — | — |
| | | | | 33 | — | — | — | 102 | 0.90 | 1.09 |
| | | | | 143 | 99 | 71 | 77 | 120 | 0.89 | 0.92 |
| | | | | 303 | — | — | — | 102 | — | — |
| | | | | 346 | — | — | — | — | 0.95 | 0.91 |
| | | | | 364 | 101 | 68 | 74 | — | — | — |
| | | | | 564 | — | — | — | — | 0.93 | 1.07 |
| | | | | 810 | 89 | 55 | 62 | 112 | 1.07 | 1.06 |
| | | | | 922 | — | — | — | — | 0.97 | 1.05 |
| | | | | 924 | 86 | 54 | 59 | — | 0.87 | 0.99 |
| | | | | 1125 | — | — | — | 140 | 1.01 | 1.03 |
| | | | | 1285 | — | — | — | 140 | 1.25 | 1.12 |
| | | | | 1488 | — | — | — | — | 1.19 | 1.16 |
| B04 | F | 54 | 56 | 0 | 89 | 79 | 66 | — | — | — |
| | | | | 242 | 88 | 63 | 62 | — | — | — |
| | | | | 324 | 85 | 61 | 57 | — | — | — |
| | | | | 601 | 70 | 53 | 52 | — | — | — |
| | | | | 846 | 60 | 53 | 49 | — | — | — |
| A05 | F | 62 | 62.5 | 0 | 112 | 85 | 77 | — | — | — |
| | | | | 551 | 100 | 75 | 61 | — | — | — |
| | | | | 800 | 86 | 71 | 61 | — | — | — |
| | | | | 1017 | 80 | 58 | 57 | — | — | — |
| 06 | F | 57 | 64 | 0 | 90 | 69 | 60 | 89 | 1.04 | 1.03 |
| | | | | 228 | — | — | — | 115 | 1.22 | 1.11 |
| | | | | 271 | — | — | — | 110 | 1.00 | 0.95 |
| | | | | 273 | 83 | 64 | 55 | 104 | 1.04 | 0.97 |
| | | | | 277 | — | — | — | 94 | 1.29 | 1.14 |
| | | | | 280 | — | — | — | 94 | 1.22 | 1.05 |
| | | | | 281 | — | — | — | 98 | 1.26 | 1.11 |
| | | | | 285 | — | — | — | 90 | 1.00 | 0.96 |
| | | | | 286 | — | — | — | 92 | 1.01 | 0.90 |
| | | | | 288 | — | — | — | 98 | 1.03 | 1.03 |
| | | | | 739 | — | — | — | nt | 1.35 | 1.17 |
| 07 | F | 62 | 65 | 0 | — | — | — | — | 0.84 | 0.77 |
| | | | | 77 | 60 | 60 | 53 | — | — | — |
| | | | | 136 | — | — | — | 135 | — | — |
| | | | | 257 | 51 | 56 | 49 | 135 | 1.61 | 1.73 |
| | | | | 586 | — | — | — | nt | — | — |
| 08 | F | 64 | 65.5 | 0 | 83 | 68 | 63 | — | — | — |
| | | | | 114 | — | — | — | — | 1.35 | 1.16 |
| | | | | 287 | 70 | 62 | 60 | — | 1.35 | 1.23 |
| B09 | F | 64 | 65.5 | 0 | 66 | 73 | 60 | — | — | — |
| | | | | 1745 | — | — | — | — | 1.84 | 1.71 |
| | | | | 2465 | — | — | — | — | 1.74 | 1.81 |
| | | | | 2677 | — | — | — | — | 1.73 | 1.96 |
| | | | | 2964 | — | — | — | — | 2.26 | 2.22 |
| | | | | 3118 | — | — | — | — | 2.25 | 1.98 |
| 10 | F | 66 | 69 | 0 | 91 | 79 | 67 | — | — | — |
| | | | | 299 | 92 | 78 | 63 | — | — | — |
| | | | | 315 | — | — | — | — | 0.71 | 0.76 |
| 11 | M | 69 | 72 | 0 | 78 | 68 | 55 | — | 1.35 | 1.29 |
| | | | | 43 | — | — | — | — | 1.21 | 1.31 |
| | | | | 175 | — | — | — | 120 | 1.22 | 1.49 |
| | | | | 475 | — | — | — | — | 1.79 | 1.75 |
| | | | | 607 | 57 | 40 | 49 | 120 | 1.89 | 1.88 |

TABLE 1B

| Patient | Sex | Age of Onset | Age at First Observation | Day of Observation | WAIS Verbal | WAIS Performance | Wechsler Memory | Backward Masking (msec) | Theta:Alpha C3-Pz | Theta:Alpha C4-Pz | Desferioxamine Dose | Desferioxamine Schedule |
|---|---|---|---|---|---|---|---|---|---|---|---|---|
| 12 | F | 53 | 55.5 | 0 | 60 | 95 | 62 | 108 | 0.31 | 0.40 | | |
| | | | | 32 | — | — | — | — | — | — | 0.5g b.i.d. | 21/21 |
| | | | | 87 | 63 | 92 | 64 | 85 | 0.31 | 0.32 | | |
| | | | | 213 | — | — | — | — | — | — | 0.5g o.d. | 21/21 |
| | | | | 240 | 64 | 88 | 67 | — | 0.29 | 0.27 | | |
| | | | | 430 | 57 | 82 | 64 | 110 | 0.33 | 0.33 | | |
| | | | | 520 | — | — | — | 110 | — | — | | |
| | | | | 625 | 54 | 92 | 59 | — | 0.29 | 0.32 | | |
| | | | | 727 | — | — | — | — | — | — | STOP | |
| | | | | 815 | 54 | 89 | 54 | nt | 0.30 | 0.33 | | |
| | | | | 961 | 46 | 68 | 48 | nt | 0.34 | 0.32 | | |
| B13 | F | 53 | 55.5 | 0 | 74 | 65 | 59 | — | — | — | | |
| | | | | 175 | 73 | 59 | 55 | — | — | — | | |
| | | | | 219 | — | — | — | — | — | — | 0.5g b.i.d. | 28/28 |
| | | | | 279 | — | — | — | — | — | — | 0.5g o.d. | 28/28 |

TABLE 1B-continued

| Patient | Sex | Age of Onset | Age at First Observation | Day of Observation | WAIS Verbal | WAIS Performance | Wechsler Memory | Backward Masking (msec) | Theta:Alpha C3-Pz | Theta:Alpha C4-Pz | Desferioxamine Dose | Desferioxamine Schedule |
|---|---|---|---|---|---|---|---|---|---|---|---|---|
| | | | | 370 | 70 | 59 | 49 | — | — | — | | |
| | | | | 572 | 57 | 53 | nt | — | — | — | STOP | |
| | | | | 685 | — | — | — | — | 1.75 | — | | |
| | | | | 872 | — | — | — | — | 2.17 | 1.85 | | |
| | | | | 1069 | — | — | — | — | nt | 2.00 | | |
| 14 | M | 57 | 62.5 | 0 | — | — | — | — | 0.97 | 0.80 | | |
| | | | | 35 | 114 | 78 | 79 | — | — | — | | |
| | | | | 105 | — | — | — | 110 | 1.11 | 1.11 | | |
| | | | | 154 | — | — | — | 110 | 1.31 | 1.30 | | |
| | | | | 175 | — | — | — | — | — | — | 0.5g b.i.d. | 21/14 |
| | | | | 244 | — | — | — | 95 | 1.10 | 0.97 | | |
| | | | | 405 | 108 | 72 | 79 | 86 | 1.22 | 1.06 | | |
| | | | | 546 | 106 | 65 | 80 | — | 1.27 | 1.05 | | |
| 15 | F | 48 | 54 | 0 | 58 | nt | nt | 120 | 1.41 | 1.37 | 0.5g o.d. | daily |
| | | | | 103 | — | — | — | 150 | 1.56 | 1.35 | 0.5g b.i.d. | daily |
| | | | | 216 | 50 | nt | nt | 140 | 1.49 | 1.39 | STOP | |
| | | | | 334 | — | — | — | nt | 1.52 | 1.39 | | |
| | | | | 337 | — | — | — | — | 1.52 | 1.56 | | |
| | | | | 340 | — | — | — | — | 1.71 | 1.64 | | |
| | | | | 373 | — | — | — | — | 1.60 | 1.54 | | |
| 16 | M | 49 | 53 | 0 | — | — | — | 126 | 1.18 | 1.36 | | |
| | | | | 429 | 90 | nt | 59 | 130 | 1.83 | 1.90 | | |
| | | | | 535 | 91 | nt | 60 | — | 1.81 | 1.78 | | |
| | | | | 611 | — | — | — | — | — | — | 0.5g b.i.d. | 21/14 |
| | | | | 702 | — | — | — | nt | 1.81 | 2.23 | | |
| | | | | 772 | 75 | nt | 54 | nt | 1.70 | 1.71 | | |
| | | | | 794 | — | — | — | — | — | — | STOP | |
| | | | | 922 | — | — | — | — | 1.70 | 1.62 | | |
| | | | | 1344 | — | — | — | — | nt | nt | | |
| 17 | M | 56 | 61.5 | 0 | 88 | 54 | 66 | — | — | 1.81 | | |
| | | | | 379 | 82 | nt | 60 | 155 | 1.88 | 1.81 | | |
| | | | | 380 | — | — | — | — | 2.10 | 2.06 | 0.5g b.i.d. | 21/14 |
| | | | | 462 | 72 | nt | 55 | — | — | — | | |
| | | | | 481 | — | — | — | — | 2.23 | 1.96 | | |
| | | | | 559 | 70 | nt | 54 | 180 | 2.11 | 1.71 | STOP | |
| | | | | 683 | — | — | — | 122 | 1.95 | 1.74 | | |
| | | | | 871 | — | — | — | 100 | 1.94 | 1.80 | | |

TABLE 2

| | Tests of Cognitive Function Improved | No Change | Deteriorated |
|---|---|---|---|
| (A) Verbal | | | |
| Control | 0 | .20 | .80 |
| Treated | .08 | .31 | .67 |
| (B) Performance | | | |
| Control | .05 | .20 | .75 |
| Treated | .17 | .17 | .67 |
| (C) Memory | | | |
| Control | .04 | .09 | .87 |
| Treated | .18 | .17 | .67 |

Legend:
Probability of outcome for control (n = 12) and treated (n = 6) groups on Wechsler Adult Intelligence and Memory Tests. Table based on 100 data points. Mean test interval for control group 8.8 ± 4.2 SD months, treated group 5.5 ± 1.85 SD months.

TABLE 3

| | Patient Number | Test Interval (days) | Identification Before | Threshold (msec) During |
|---|---|---|---|---|
| Control | | | | |
| | 01 | 484 | 80 | 118 |
| | 02 | 286 | 100 | 160 |
| | 03 | 270 | 102 | 111 |
| | 06 | 288 | 89 | 99 |
| | 07 | 120 | 135 | 135 |
| | 11 | 432 | 120 | 120 |
| Mean | | | | |
| | | 313 | 104 | 124 |
| Treated | | | | |
| | 12 | 520 | 108 | 102 |
| | 14 | 300 | 110 | 89 |
| | 15 | 216 | 120 | 145 |

TABLE 3-continued

| | Patient Number | Test Interval (days) | Identification Before | Threshold (msec) During |
|---|---|---|---|---|
| | 16 | — | 130 | NT |
| | 17 | 180 | 155 | 180 |
| Mean | | | | |
| | | 304 | 125 | 129 |

Legend:
Tachistoscopic Letter Identification Thresholds in the Presence of a Backward Pattern Mask

TABLE 4

| | | Theta to Alpha Ratio Improved | No Change | Deteriorated |
|---|---|---|---|---|
| (A) Left | | | | |
| | Control (n = 10) | 0.02 ± 0.06 | 0.21 ± 0.24 | 0.78 ± 0.22 |
| | Treated (n = 5) | 0.24 ± 0.32 | 0.50 ± 0.29 | 0.27 ± 0.32 |
| (B) Right | | | | |
| | Control (n = 11) | 0.03 ± 0.06 | 0.19 ± 0.25 | 0.78 ± 0.28 |
| | Treated (n = 5) | 0.26 ± 0.29 | 0.49 ± 0.31 | 0.25 ± 0.26 |
| (C) Both | | | | |
| | Control (n = 10) | 0.03 ± 0.04 | 0.18 ± 0.22 | 0.79 ± 0.23 |
| | Treated (n = 5) | 0.25 ± 0.30 | 0.52 ± 0.27 | 0.26 ± 0.26 |

Legend:
Probability of change in $\theta:\alpha$ ratio of electroencephalogram; mean inter-observation period for control group 335 ± 114 SD days and treated group 302 ± 111 SD days.

TABLE 5

| Patient Age | Desferoxamine Urinary Excretion Al (500 mg Bid) Before ug Al/24 hr | After ug Al/24 hr | Change % |
|---|---|---|---|
| 70 | 12 | 28 | 240 |
| 66 | 33.2 | 114 | 360 |
| 59 | 55 | 122 | 220 |
| 59 | 16 | 44 | 280 |
| 59 | 53 | 156 | 290 |
| Mean | 34 | 93 | 270 |

What is claimed is:

1. A method of treating Alzheimer's disease which comprises parenterally administering to a person requiring such treatment an aqueous solution of about 0.2 to about 5.0 daily of a pharmaceutically acceptable acid addition salt of deferoxamine.

2. A method according to claim 1 which comprises parenterally administering an aqueous solution of about 0.2 to about 1.5 g daily of a pharmaceutically acceptable acid addition salt of deferoxamine.

3. A method according to claim 1 which comprises parenterally administering an aqueous solution of about 0.5 to about 1.0 g daily of a pharmaceutically acceptable acid addition salt of deferoxamine.

4. A method according to claim 1 which comprises parenterally administering twice daily an aqueous solution of 0.5 g of pharmaceutically accpetable acid addition salt of deferoxamine.

5. A method according to claim 1 in which the aqueous solution of a pharmaceutically acceptable acid addition salt of deferoxamine is administered intramuscularly.

6. A method according to claim 1 in which pharmaceutically acceptable acid addition salt of deferoxamine used is the mesylate.

* * * * *